United States Patent [19]
Atwal

[11] Patent Number: 5,563,170
[45] Date of Patent: Oct. 8, 1996

[54] SUBSTITUTED CYANOIMINO BENZOPYRANES

[75] Inventor: Karnail Atwal, Newtown, Pa.

[73] Assignee: E. R. Squibb & Sons, Inc., Princeton, N.J.

[21] Appl. No.: 745,563

[22] Filed: Aug. 15, 1991

Related U.S. Application Data

[63] Continuation-in-part of Ser. No. 502,967, Apr. 2, 1990, Pat. No. 5,061,813.
[51] Int. Cl.$^6$ .......................... A61K 31/35; A61K 31/66; A61K 31/665
[52] U.S. Cl. ............................... 514/456; 514/100
[58] Field of Search ..................... 549/404, 399, 549/345, 220; 514/456, 100

[56] References Cited

FOREIGN PATENT DOCUMENTS

| | | |
|---|---|---|
| 205292 | 12/1986 | European Pat. Off. . |
| 344747 | 12/1989 | European Pat. Off. . |
| 412531 | 2/1991 | European Pat. Off. . |

OTHER PUBLICATIONS

V. A. Ashwood et al., *J. Med. Chem.*, 1986, 29, 2194–2201.
A. Banerji et al., *Tetrahedron Letters*, No. 38, pp. 3685–3686 (1979).
J. M. Evans et al., *J. Med. Chem.*, 1983, 26, 1582–1589.
R. W. Lang et al., *Helvetica Chimica Acta.*, vol. 71 (1988) pp. 596–601.
G. Ariamala et al., *Tetrahedron Letters*, vol. 29, No. 28, pp. 3487–3488 (1988).
P. Sebok et al., *Heterocycles*, vol. 27, No. 11, 1988, pp. 2595–2607.
P. Teixidor et al., *Heterocycles*, vol. 27, No. 10 (1988) pp. 2459–2465.

*Primary Examiner*—Nicky Chan
*Attorney, Agent, or Firm*—Theodore R. Furman, Jr.; Ellen K. Park

[57] ABSTRACT

Novel compounds are disclosed having the formula

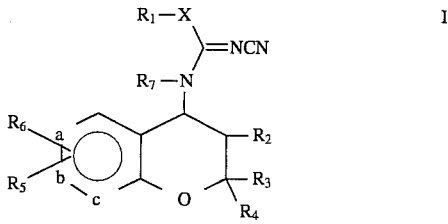

and $R_1$, $R_2$, $R_3$, $R_4$, $R_5$, $R_6$ and $R_7$ are as defined herein. These compounds are useful, for example, as cardiovascular agents and especially as anti-ischemic agents.

5 Claims, No Drawings

SUBSTITUTED CYANOIMINO BENZOPYRANES

This is a continuation-in-part of U.S. Ser. No. 502,967, filed Apr. 2, 1990, now U.S. Pat. No. 5,061,813.

FIELD OF THE INVENTION

The present invention relates to novel compounds having potassium channel activating activity which are therefore useful, for example, as cardiovascular agents.

SUMMARY OF THE INVENTION

In accordance with the present invention novel compounds having potassium channel activating activity which are useful, for example, as cardiovascular agents, are disclosed. These compounds have the general formula

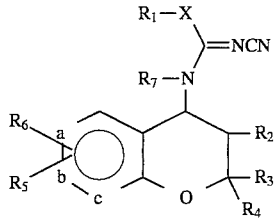

wherein a, b, and c are all carbons or one of a, b and c can be nitrogen or —NO— and the others are carbons;
where X is oxygen or sulfur;

$R_1$ is selected from aryl, arylalkyl, (heterocyclo)alkyl, heterocyclo, cycloalkyl and (cycloalkyl)alkyl.

$R_2$ is hydrogen, hydroxy,

$R_3$ and $R_4$ are each independently hydrogen, alkyl or arylalkyl, or, $R_3$ and $R_4$ taken together with the carbon atom to which they are attached form a 5- to 7-membered carbocyclic ring;

$R_5$ is selected from H, alkyl, haloalkyl, alkenyl, alkynyl, cycloalkyl, arylalkyl, cycloalkylalkyl, —CN, —NO₂, —COR, —COOR, —CONHR, —CONR₂, —CF₃, S-alkyl, —SOalkyl, —SO₂alkyl,

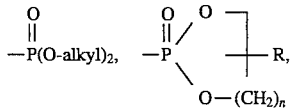

halogen, amino, substituted amino, O-alkyl, OCF₃, OCH₂CF₃, —OCOalkyl, —OCONRalkyl, —NRCOalkyl and NRCOOalkyl, NRCONR₂ wherein R in each of the above groups can be hydrogen, alkyl, aryl, arylalkyl, cycloalkyl, or (cycloalkyl)alkyl;

$R_6$ is selected from H, alkyl, OH, O-alkyl, amino, substituted amino, CN, and NO₂;

$R_7$ is selected from hydrogen, alkyl, alkenyl, aryl, arylalkyl, cycloalkyl or cycloalkylalkyl; and, n is 1, 2 or 3.

DETAILED DESCRIPTION OF THE PRESENT INVENTION

This invention in its broadest aspects relates to the cyanoguanidine compounds of formula I above, to compositions and the methods of using such compounds. The compounds of formula I are useful, for example, as cardiovascular agents. Preferred compounds are those with the 3S, 4R stereochemistry.

The term "alkyl" used in defining various symbols refers to straight or branched chain saturated hydrocarbon radicals having up to eight carbons, preferably from one to five carbons. Similarly, the terms "alkoxy" and "alkylthio" refer to such alkyl groups attached to an oxygen or sulfur.

The term "alkenyl" refers to straight or branched chain hydrocarbon radicals having from two to eight carbons and one double bond, preferably three to five carbons. The term "alkynyl" refers to straight or branched chain hydrocarbon radicals having from two to eight carbons and one triple bond, preferably three to five carbons.

The term "cycloalkyl" refers to saturated carbocyclic rings of 4 to 7 carbon atoms with cyclopentyl and cyclohexyl being most preferred.

The term "halo" or "halogen" refers to chloro, bromo and fluoro.

The term "halo substituted alkyl" refers to such alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term "aryl" refers to phenyl, 1-naphthyl, 2-naphthyl or mono substituted phenyl, 1-naphthyl, 2-naphthyl wherein said substituent is alkyl of 1 to 4 carbons, alkylthio of 1 to 4 carbons, alkoxy of 1 to 4 carbons, halo, nitro, cyano, hydroxy, amino, —NH-alkyl wherein alkyl is of 1 to 4 carbons, —N(alkyl)₂ wherein alkyl is of 1 to 4 carbons,

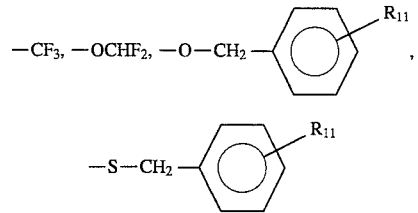

(wherein $R_{11}$ is hydrogen, alkyl of 1 to 4 carbons, alkoxy of 1 to 4 carbons, alkylthio of 1 to 4 carbons, halo, hydroxy or CF₃), —O—CH₂-cycloalkyl, or —S—CH₂— cycloalkyl, and di-substituted phenyl, 1-naphthyl, 2-naphthyl wherein said substituents are selected from methyl, methoxy, methylthio, halo, CF₃, nitro, amino, and OCHF₂.

Preferred aryl groups include unsubstituted phenyl and monosubstituted phenyl wherein the substituents are nitro, halo, —CF₃, alkyl, cyano or methoxy.

The term "heterocyclo" refers to fully saturated or unsaturated rings of 5 or 6 atoms containing one or two O and S atoms and/or one to four N atoms provided that the total number of hetero atoms in the ring is 4 or less. The hetero ring is attached by way of an available carbon atom. Preferred monocyclic hetero groups include 2- and 3-thienyl, 2- and 3-furyl, 2-, 3- and 4-pyridyl, and imidazolyl. The term hetero also includes bicyclic rings wherein the five or six membered ring containing O, S and N atoms as defined above is fused to a benzene ring and the bicyclic ring is attached by way of an available carbon atom. Preferred bicyclic hetero groups include 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofuranzanyl.

The term heterocyclo also includes such monocyclic and bicyclic rings wherein an available carbon atom is substituted with a lower alkyl of 1 to 4 carbons, lower alkylthio of 1 to 4 carbons, lower alkoxy of 1 to 4 carbons, halo, nitro, keto, cyano, hydroxy, amino, —NH-alkyl wherein alkyl is of 1 to 4 carbons, -N(alkyl)$_2$ wherein alkyl is of 1 to 4 carbons, $CF_3$, or $OCHF_2$ or such monocyclic and bicyclic rings wherein two or three available carbons have substituents selected from methyl, methoxy, methylthio, halo, $CF_3$, nitro, hydroxy, amino and $OCHF_2$.

The term "substituted amino" refers to a group of the formula —$NZ_1Z_2$ wherein $Z_1$ is hydrogen, alkyl, cycloalkyl, aryl, arylalkyl, cycloalkylalkyl and $Z_2$ is alkyl, cycloalkyl, aryl, arylalkyl, cycloalkylalkyl or $Z_1$ and $Z_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl substituted with alkyl, alkoxy, alkylthio, halo, trifluoromethyl or hydroxy.

The compounds of formula I can be prepared by reacting a compound of the formula

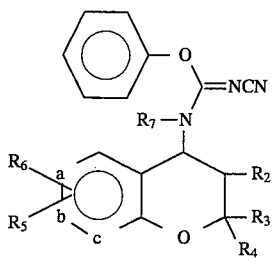

II with a compound of the formula

III in a solvent and in the presence of a base, such as potassium carbonate, triethylamine, and the like. The compounds of formula II are prepared by reacting an amine of the formula

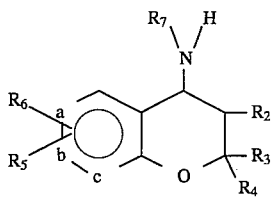

IV with diphenylcyanocarbonimidate.

The amine of formula IV where $R_2$ is hydroxy can be prepared by methods described in the literature, such as by J. M. Evans, C. S. Fake, T. C. Hamilton, R. H. Payser and E. A. Watts, *J. Med. Chem.*, 1983, 26, 1582 and *J. Med. Chem.*, 1986, 29, 2194; R. W. Lang, P. F. Wenk, *Helvetica Chimica Acta.*, 1988, 71, 596; EP 0,205,292 A2 (1986), and WO 87/07607.

The amine of formula IV when $R_2$ is hydrogen can be prepared from a ketone of the formula

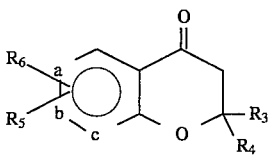

V by standard methodology. The ketone of formula V can be obtained by literature procedures such as those disclosed by P. Sebok and T. Timar, *Heterocycles*, 1988, 27, 2595; P. Teixidor et al., *Heterocycles*, 1988, 27, 2459; A. Benerji and N. C. Goomer, *Tetrahedron Letters*, 1979, 3685; G. Ariamala and K. K. Subramanian, *Tetrahedron Letters*, Vol. 29, 28,p. 3487–3488 (1988).

The compounds of the present invention wherein $R_2$ is OCOalkyl can be prepared by acylation of the alcohol of formula I, wherein $R_2$ is OH, with an acid chloride of the formula

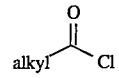

VI in the presence of a base catalyst, such as pyridine or triethylamine.

Preferred compounds are those wherein $R_1$ is aryl, arylalkyl;

$R_2$ is hydroxy;

$R_3$ and $R_4$ are each alkyl;

$R_5$ is an electron withdrawing group;

$R_6$ is hydrogen, alkyl, O-alkyl, amino; and, $R_7$ is hydrogen.

Most preferred are those compounds wherein $R_1$ is phenyl, phenylmethyl;

$R_2$ is trans-hydroxy;

$R_3$ and $R_4$ are each methyl;

$R_5$ is —CN or —$NO_2$;

$R_6$ is hydrogen;

$R_7$ is hydrogen; and,

X is sulfur.

The compounds of the present invention can have asymmetric centers at carbons 2–4 of benzopyran ring. Also, any one of the R's can have an asymmetric carbon. Consequently, compounds of formula I can exist in diastereomeric forms or in mixtures thereof. The above described process can utilize racemates, enantiomers or diastereomers as starting materials. When diastereomeric products are prepared, they can be separated by conventional chromatographic or fractional crystallization methods.

The compounds of the present invention wherein $R_7$ is hydrogen, can exist as a mixture of tautomers represented by the following structures. The tautomeric products are obtained in relative amounts that differ from compound to compound. All forms are included in the scope of formula I.

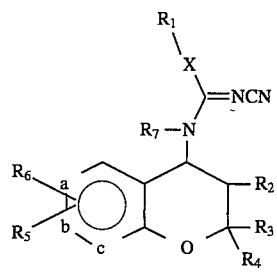

I'

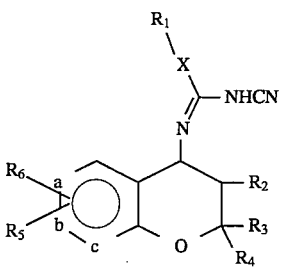

I"

The compounds of formula I and the pharmaceutically acceptable salts act as potassium channel activators. Thus, compounds of the present invention are useful as antiarrhythmic agents and as antiischemic agents.

It has been found that compounds of formula I are particularly useful as antiischemic agents, i.e., for the treatment of ischemic conditions such as myocardial ischemia, cerebral ischemia, lower limb ischemia and the like. Unexpectedly, these compounds have been found to be "selective" antiischemic agents in that they possess little or no vasodilator activity and have little or no effect on blood pressure. This means that in the treatment of, for example, ischemic heart, these compounds are less likely to cause coronary steal, profound hypotension and coronary underperfusion.

The preferred antiischemic agents of this invention are those wherein $R_1$ is aryl or arylalkyl and $R_7$ is hydrogen.

Thus, by the administration of a composition containing one (or a combination) of the compounds of this invention ischemic conditions of a mammalian (e.g., human) host are reduced. A single dose, or preferably two to four divided daily doses, provided on a basis of about 0.001 to 100 mg per kilogram of body weight per day, preferably from about 0.1 to about 25 mg per kilogram per day, is appropriate to reduce ischemic conditions. The substance is preferably administered orally, but parenteral routes, such as the subcutaneous, intramuscular, or intravenous routes or any other convenient delivery system, such as inhalation or intranasal solutions or transdermal patches, can also be employed. The above doses are also suitable for the other cardiovascular and noncardiovascular uses.

As a result of the potassium channel activating activity of compounds of this invention, these compounds are also useful in the treatment of cardiovascular disorders and any disorders associated with smooth muscle contraction. For example, compounds of the present invention are useful as therapy for congestive heart failure, therapy for peripheral vascular disorders (e.g. Raynaud's Disease), therapy for pulmonary hypertension, as anti-anginal agents, as anti-fibrillatory agents, as thrombolytic agents and in limiting myocardial infarction.

Compounds of the present invention are additionally expected to be useful in the treatment of central nervous system disorders (e.g., Parkinsonism, as anti-tremor agents, epilepsy), in therapy for renal failure, in therapy for urinary incontinence, as anti-diarrheal agents, in therapy for pre-eclampsia, dysmenorrhea and premature labor, as well as for the promotion of hair growth (e.g., in the treatment of male pattern baldness) and as anti-asthmatic agents.

The compounds of this invention can also be formulated in combination with a diuretic such as, chlorothiazide, hydrochlorothiazide, flumethiazide, hydroflumethiazide, bendroflumethiazide, methylchlothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or calcium channel blocking agents such as nifedipine or diltiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The present invention will now be described by the following examples, however, the invention should not be limited to the details therein.

EXAMPLE 1

(trans)-4-[[(Cyanoimino)phenoxymethyl]amino]-3,4-dihydroxy-2,2-dimethyl-2H-1-benzopyran-6-carbonitrile To a solution of (trans)-4-amino-3,4-dihydro-3-hydroxy-2,2-dimethyl-2H-1-benzopyran-6-carbonitrile (prepared according to Evans et al., *J. Med. Chem.*, 1983, 26, 1582 and *J. Med. Chem.*, 1986, 29, 2194) (5.0 g, 23 mmol) in isopropanol (50 mL), diphenylcyanocarbonimidate (5.5 g, 25 mmol) was added at room temperature and the reaction mixture was allowed to stir at room temperature for 16 hours. Most of the isopropanol was evaporated and the residue was dissolved in ethyl acetate. The resulting solution was washed successively with 10% citric acid, 1 N sodium hydroxide solution and brine. It was dried over anhydrous magnesium sulfate, concentrated and the residue was crystallized from chloroform-isopropyl ether to yield the title A compound (4.2 g) as a colorless solid, m.p. 186°–188° C.

Analysis calc'd for $C_{20}H_{18}N_4O_3 \cdot 0.6H_2O$: C, 64.37; H, 5.18; N, 15.02; Found: C, 64.64; H, 4.86; N, 14.75.

EXAMPLE 2

(trans)-N"-Cyano-N-(6-cyano-3,4-dihydro-3-hydroxy-2,2-dimethyl-2H-1-benzopyran-4-yl) carbamimidothioic acid, phenyl ester A suspension of the title compound of Example 1 (1.0 g, 2.8 mmol) in isopropanol (6 ml) was treated at room temperature with diisopropylethylamine (0.4 g, 3.3 mmol) followed by thiophenol (0.36 g, 3.3 mmol). The reaction was allowed to stir at room temperature for 20 hours and concentrated in vacuo. The residue was purified by flash chromatography on silica gel eluting with hexane-ethyl acetate (1:1) to give a white solid (0.5 g). The product was crystallized from isopropanol-ether to give the title compound as a colorless solid, m.p. 191°–192° C.

Analysis calc'd for $C_{20}H_{18}N_4O_2S$: C, 63.47; H, 4.79; N, 14.81; S, 8.47; Found: C, 63.35; H, 4.67; N, 14.58; S, 8.53.

EXAMPLES 3–11

The following compounds within the scope of the present invention can also be prepared using the methodology described above.

Ex. 3

Ex. 4

Ex. 5

Ex. 6

Ex. 7

Ex. 8

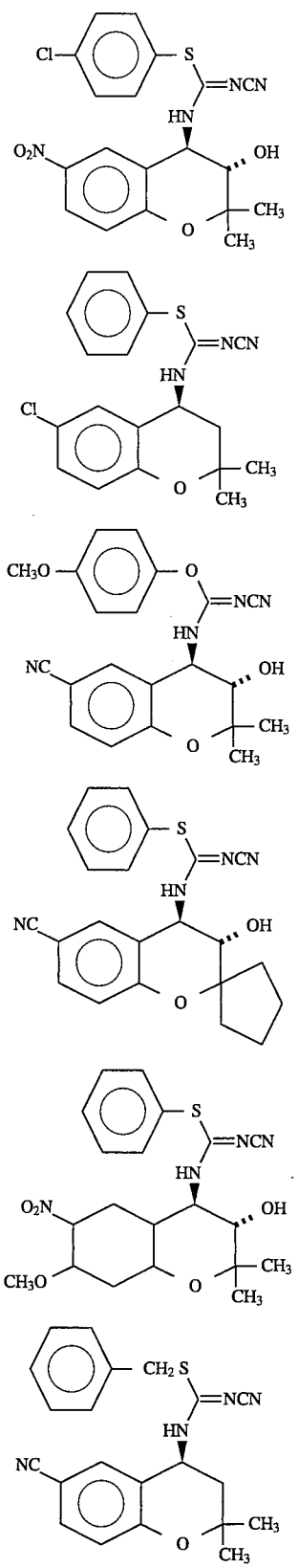

Ex. 9

Ex. 10

Ex. 11

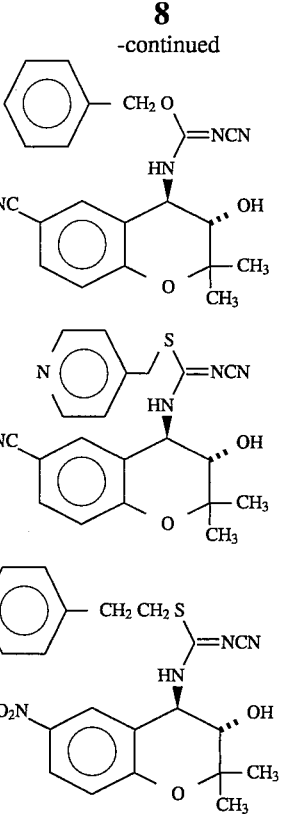

What is claimed is:

1. A method for the treatment of ischemic conditions in mammals comprising administering to a mammalian specie in need thereof a therapeutically effective amount of a compound of the formula

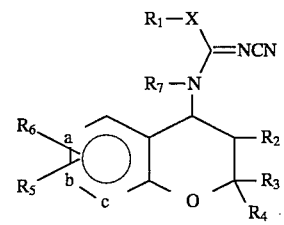 I wherein a, b, and c are all carbons;

R$_1$ is selected from aryl, arylalkyl, cycloalkyl and (cycloalkyl)alkyl;

where X is oxygen or sulfur;

R$_2$ is hydrogen, hydroxy or

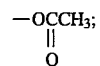

R$_3$ and R$_4$ are each independently hydrogen, alkyl or arylalkyl, or, R$_3$ and R$_4$ taken together with the carbon atom to which they are attached form a 5- to 7-membered carbocyclic ring;

R$_5$ is selected from H, alkyl, haloalkyl, alkenyl, alkynyl, cycloalkyl, arylalkyl, cycloalkylalkyl, —CN, —NO$_2$, —COR, —COOR, —CONHR, —CON(R)$_2$, S-alkyl, —SOalkyl, —SO$_2$alkyl,

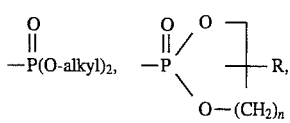

halogen, amino, substituted amino, O-alkyl, $OCF_3$, $OCH_2CF_3$, —OCOalkyl, —OCONRalkyl, —NRCOalkyl and NRCOOalkyl, —NRCON(R)$_2$ wherein R in each of the above groups can be hydrogen, alkyl, aryl, arylalkyl, cycloalkyl, or (cycloalkyl)alkyl;

$R_6$ is selected from H, alkyl, OH, O-alkyl, amino, substituted amino, CN, and $NO_2$;

$R_7$ is selected from hydrogen, alkyl, alkenyl, aryl, arylalkyl, cycloalkyl or cycloalkylalkyl; and n is 1, 2 or 3.

2. A method in accordance with claim 1 wherein $R_1$ is aryl, arylalkyl;

$R_2$ is hydroxy;

$R_3$ and $R_4$ are each alkyl;

$R_5$ is —CN or $NO_2$;

$R_6$ is hydrogen, alkyl, O-alkyl, amino; and, $R_7$ is hydrogen.

3. A method in accordance with claim 1 wherein $R_1$ is phenyl or phenylmethyl;

$R_2$ is trans-hydroxy;

$R_3$ and $R_4$ are each methyl;

$R_5$ is —CN or —$NO_2$;

$R_6$ is hydrogen;

$R_7$ is hydrogen;

X is sulfur; and, n is 1.

4. A method in accordance with claim 1 wherein the compound has (trans)-4-[[(cyanoimino)phenoxymethyl]amino]-3,4-dihydro-2,2-dimethyl-2H-1-benzopyran-6-carbonitrile.

5. A method in accordance with claim 1 wherein the compound has the name (trans)-N"-cyano-N-(6-cyano-3,4-dihydro-3-hydroxy-2,2-dimethyl-2H-1-benzopyran-4-yl) carbamimidothioic acid, phenyl ester.

* * * * *